United States Patent
Jalkanen et al.

(10) Patent No.: US 11,421,279 B2
(45) Date of Patent: Aug. 23, 2022

(54) METHOD FOR DETERMINING PATIENT'S RESPONSIVENESS TO TYPE 1 INTERFERON TREATMENT AND USE OF TYPE 1 INTERFERON TO TREAT PATIENT HAVING SPECIFIED SINGLE NUCLEOIDE POLYMOPHISM

(71) Applicant: Faron Pharmaceuticals Oy, Turku (FI)

(72) Inventors: Juho Jalkanen, Mietoinen (FI);
Markku Jalkanen, Piispanristi (FI);
Matti Karvonen, Turku (FI)

(73) Assignee: Faron Pharmaceuticals Oy, Turku (FI)

( * ) Notice: Subject to any disclaimer, the term of this patent is extended or adjusted under 35 U.S.C. 154(b) by 19 days.

(21) Appl. No.: 16/703,243

(22) Filed: Dec. 4, 2019

(65) Prior Publication Data

US 2020/0199677 A1 Jun. 25, 2020

(30) Foreign Application Priority Data

Dec. 4, 2018 (FI) .................................... 20186041

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

| JP | 4295955 B2 | 7/2009 |
| WO | 2010010057 A2 | 1/2010 |

OTHER PUBLICATIONS

NCBI SNP Database for rs9984273, available via URL <ncbi.nlm.nih.gov/snp/rs9984273?vertical_tab=true>, printed on Jul. 27, 2021. (Year: 2021).*
Li et al (BMC Genetics. 2010. 11: 47, p. 1-9 (Year: 2010).*
Zill et al. Molecular Psychiatry. 2004. 9: 1030-1036 (Year: 2004).*
Langdahl et al Journal of Bone and Mineral Research (2000) 15: 402-414 (Year: 2000).*
Wall et al. Nature Reviews Genetics. 2003. 4:587-597 (Year: 2003).*
Bellingan, G. et al. A phase III double-blind, randomised, parallel-group comparison of the efficacy and safety of FP-1201-LYO (recombinant human interferon beta-1 A) and placebo in the treatment of patients with moderate or severe acute respiratory distress syndrome. 31st ESICM Conference, Paris, [online], Oct. 22, 2018, pp. 1-27.
Comabella, M. et al. Genome-wide Scan of 500 000 Single-Nucleotide Polymorphisms Among Responders and Nonresponders to Interferon Beta Therapy in Multiple Sclerosis. Archives of Neurology, Aug. 2009, vol. 66, No. 8, pp. 972-978.
Song, Q.-M. et al. Association study of IFNAR2 and IL 10RB genes with the susceptibility and interferon response in HBV infection. Journal of Viral Hepatitis, Sep. 2009, vol. 16, No. 9, pp. 674-680.
Welzel, T. M. et al. Variants in interferon-alpha pathway genes and response to pegylated interferon-alpha2a plus ribavirin for treatment of chronic hepatitis C virus infection in the hepatitis C antiviral long-term treatment against cirrhosis trial. Hepatology, Jun. 2009, vol. 49, No. 6, pp. 1847-1858.
Bellingan et al., Comparison of the efficacy and safety of FP-1201-lyo (intravenously administered recombinant human interferon beta-1a) and placebo in the treatment of patients with moderate or severe acute respiratory distress syndrome: study protocol for a randomized controlled trial, Trials (2017) 18:536.
Bellingan et al., The effect of intravenous interferon-beta-1a(FP-1201) on lung CD73 expression and on acute respiratory distress syndrome mortality: an open-label study, Lancet Respiratory Med, 2014, 2: 98-107.
Flammer et al., The Type I Inerferon Signaling Pathway is a Target for Glucocorticoid Inhibition, Molecular and Cellular Biology, Oct. 2010, vol. 30, No. 19, pp. 4564-4574.
Jalkanen et al., VAP-1 and CD73, Endothelial Cell Surface Enzymes in Leukocyte Extravasation, Arteriosclerosis, Thromosis, and Vascular Biology, 2008: 28: 18-26.
Kiss et al., IFN-β protects from vascular leakage via up-regulation of CD73, Eur. J. Immunol. 2007, 37, pp. 3334-3338.
Levy et al., Ringing the interferon alarm: differential regulation of gene expression at the interface between innate and adaptive immunity, Current Opinion in Immunology, 2003, 15, pp. 52-58.
Mahurkar et al., Response to interferon-beta treatment in multiple sclerosis patients: a genome-wide association study, The Pharmacogenomics Journal, Mar. 2016, 8 pages.
Interest trial update presented at ESICM, Faron Pharmaceuticals Ltd., released Oct. 22, 2018, RNS No. 7971E, 3 pages.
Finnish Patent and Registration Office Search Report cited in FI 20186041, dated May 31, 2019, 2 pgs.

* cited by examiner

*Primary Examiner* — Carla J Myers
(74) *Attorney, Agent, or Firm* — Rothwell, Figg, Ernst & Manbeck, P.C.

(57) ABSTRACT

A method for determining a patient's responsiveness to a therapy comprising administration of type I interferon in order to make the decision to treat a patient with type I interferon and use of a SNP rs9984273 (C/T) in IFNAR2 as a marker for determining a patient's responsiveness to said therapy.

13 Claims, 4 Drawing Sheets

Specification includes a Sequence Listing.

| Type 3 Analysis of Effects | | | | Odds Ratio Estimates | | | |
|---|---|---|---|---|---|---|---|
| Effect | DF | Wald Chi-Square | P-value | Effect | Point Estimate | 95% Wald Confidence Limits | |
| cstart2 | 1 | 11.1625 | 0.0008 | cstart2 0 vs 1 | 0.131 | 0.040 | 0.432 |
| SNP | 1 | 7.6290 | 0.0057 | SNP 0 vs 1 | 5.716 | 1.659 | 19.697 |
| AP30 | 1 | 3.2115 | 0.0731 | AP30 (1 unit incr) | 1.064 | 0.994 | 1.138 |

Fig. 4

| Type 3 Analysis of Effects | | | | Odds Ratio Estimates | | | |
|---|---|---|---|---|---|---|---|
| Effect | DF | Wald Chi-Square | P-value | Effect | Point Estimate | 95% Wald Confidence Limits | |
| cstart2 | 1 | 3.5106 | 0.0610 | cstart2 0 vs 1 | 0.289 | 0.079 | 1.059 |
| SNP | 1 | 0.9225 | 0.3368 | SNP 0 vs 1 | 1.855 | 0.526 | 6.548 |
| AP30 | 1 | 2.8902 | 0.0891 | AP30 (1 unit incr) | 1.066 | 0.990 | 1.148 |

Fig. 5

METHOD FOR DETERMINING PATIENT'S RESPONSIVENESS TO TYPE 1 INTERFERON TREATMENT AND USE OF TYPE 1 INTERFERON TO TREAT PATIENT HAVING SPECIFIED SINGLE NUCLEOIDE POLYMOPHISM

CROSS REFERENCE TO RELATED APPLICATION

This application claims the benefit of Finnish Patent Application No. 20186041 filed on Dec. 4, 2018, the disclosure of which is incorporated herein in its entirety by reference.

The present application includes a Sequence Listing filed in electronic format. The Sequence Listing is entitled "3100-120_AP107638US.txt" created on Mar. 6, 2020, and is 2 bytes in size. The information in the electronic format of the Sequence Listing is part of the present application and is incorporated herein by reference in its entirety.

FIELD OF THE INVENTION

The present invention relates to a method for determining a patient's responsiveness to the therapy comprising administration of type I interferon in order to make the decision to treat a patient with type I interferon and use of specific single nucleotide polymorphism as a marker for determining patient's responsiveness to said therapy. The present invention relates also use of type I interferons to treat patients having specified single nucleotide polymorphism.

BACKGROUND OF THE INVENTION

The publications and other materials used herein to illuminate the background of the invention, and in particular, cases to provide additional details the practice, are incorporated by reference.

Type I interferons (interferon alpha and beta among others) are our first line of defence in infections (Levy et. al., 2003). As a counter measure to acute insults type I interferons enhance cell membrane and vascular integrity. Vascular leakage is an important feature in sepsis; severe respiratory viral infections, such as MERS, SARS and influenza; viral hemorrhagic fever, such as Ebola; systemic inflammatory response syndrome (SIRS) and ischemia-reperfusion injuries brought forth by major trauma or cardiovascular surgery. Type I interferons have the ability to up-regulate CD73, a molecule which yields anti-inflammatory adenosine (Jalkanen and Salmi, 2006). CD73 derived adenosine enhances endothelial barrier function and leads to the prevention of vascular leakage, the predominant pathophysiological event in acute organ injury (Kiss et. al., 2007), namely acute respiratory distress syndrome (ARDS), acute kidney injury (AKI) and multi-organ failure (MOF). Vascular leakage in acute lung injury (ARDS) allows plasma exudation into the alveolar space leading to potentially life-threatening hypoxaemia. Interferon beta-1a has been shown to reduce the impact of ARDS by reducing vascular leakage (Bellingan et. al., 2014).

As with all protein-based biopharmaceuticals, one major obstacle that must be overcome in the use of type I interferons, such as interferon alpha or beta as a therapeutic agent is its bioactivity in an individual and exerting its anticipated effects. Genetic difference in molecular pathways threaten polypeptide activity and efficacy in pharmaceuticals. Some of these changes are known to lead to the loss or reduction of the pharmaceutical bioactivity of the protein of interest. When small amounts of hormone peptides are administered, it is also crucial that the patient is responsive to the treatment.

Type I interferons are also widely used in the treatment of multiple sclerosis (MS), but over 50% of patients do not respond to the treatment. The reason for this is unknown (Mahurkar et. al. 2016). As MS is usually a slowly progressive disease it takes in average up to 2 years to clinically determine if an MS patient is responsive to treatment or not. Means to pre-determine if a patient is responsive to interferon treatment or not are desperately needed both in MS, and also in life threating acute conditions, such as in ARDS and/or conditions associated with vascular leakage and organ dysfunction, were type I interferon could be used to enhance vascular integrity and prevent acute organ failure.

SUMMARY OF THE INVENTION

It is an object of the present invention to reduce or even eliminate the above-mentioned problems appearing in prior art.

An object of the present invention is to provide a method to make a clinical decision to treat a patient with type I interferon, and to predict an outcome and response in a disease and/or disorder requiring pharmacological intervention with type I interferon. One object is to provide a marker for use in predicting patents' responsiveness to a therapy comprising an administration of type I interferons.

By having a predictive test about the treatment response, the doctor can easily and efficiently optimize the care of the patient. Therefore, an object of the present invention is to provide a combination of a genetic test and pharmacological intervention with type I interferon to help physicians in their decision making.

Further, an object of the present invention is to provide a treatment with pharmacological intervention based on patient selection. Especially, an object of the present invention is to provide a treatment method with type I interferons to specifically identified patient group, i.e. personalized therapy.

In order to achieve among others the objects presented above, the invention is characterized by what is presented in the enclosed independent claims. Some preferred embodiments of the invention will be described in the other claims.

The embodiments and advantages mentioned in this text relate, where applicable, both to the methods and to the uses according to the invention, even though it is not always specifically mentioned.

A typical method according to the present invention is used to determine a patient's responsiveness to a therapy comprising administration of type I interferon and optionally concomitant administration of a corticosteroid, the method comprising obtaining a sample from a patient,
    determining the presence or absence of single nucleotide polymorphism (SNP) rs9984273 (C/T) in subunit 2 of the interferon alpha and beta receptor (IFNAR2) in chromosome 21 from the sample obtained from the patient, and
    classifying the patient on the grounds of the presence or absence of said SNP, wherein
      i) the presence of said SNP indicates responsiveness to the therapy, which comprises an administration of type I interferon to said patient with or without concomitant administration of corticosteroids, or ii) the absence of said SNP indicates non-responsiveness to the therapy with concomitant administration of corticosteroids and modest responsiveness to said therapy without concomitant administration of corticosteroids.

The present invention concerns also use of a single nucleotide polymorphism (SNP) rs9984273 (C/T) and/or a SNP in linkage disequilibrium with the SNP rs9984273 (C/T), in subunit 2 of the interferon alpha and beta receptor (IFNAR2) in chromosome 21, for a marker for determining a patient's responsiveness to a therapy comprising administration of type I interferon and optionally concomitant administration of corticosteroids, i.e. said SNP can be used as a marker in a selection of patients to the treatment comprising type I interferon and optionally concomitant with a corticosteroid. In a preferred embodiment of the present invention, a single nucleotide polymorphism (SNP) rs9984273 (C/T) and/or a SNP in linkage disequilibrium with the SNP rs9984273 (C/T), in subunit 2 of the interferon alpha and beta receptor (IFNAR2) in chromosome 21 is used as a marker in a selection of patients to the treatment comprising type I interferon concomitant with a corticosteroid.

Further the present invention concerns a composition comprising type I interferon as an active ingredient for use in prevention and/or treatment of a disease or a disorder requiring or beneficiating from a pharmacological intervention with type I interferon in an individual, wherein said individual has a detected single nucleotide polymorphism (SNP) rs9984273 (C/T) and/or a detected SNP in linkage disequilibrium with the SNP rs9984273 (C/T), in subunit 2 of the interferon alpha and beta receptor (IFNAR2) in chromosome 21.

Now, it has been observed that the patients receiving type I interferon treatment and having single nucleotide polymorphism (SNP) rs9984273 (C/T) in subunit 2 of the interferon alpha and beta receptor (IFNAR2) had a significantly better outcome than did the patients receiving interferon treatment without said SNP rs9984273 (C/T). The results show that SNP rs9984273 (chr 21: chr position 34635065) marker associates with the response to type I interferon therapy. The sequence containing this polymorphic marker is a glucocorticoid receptor binding site in IFNAR2 gene. In the large-scale phase III randomized placebo-controlled study, it has been observed that patients having CT instead of TT in IFNAR2 are enriched among responders and they have also better survival in ARDS. Therefore, it has been observed that SNP rs9984273 (C/T) and/or a SNP in linkage disequilibrium with the SNP rs9984273 (C/T) in IFNAR2 can be as a marker to aid a clinical decision making to start or not to start pharmacological type I interferon intervention in a patient suffering a disease or a disorder requiring or beneficiating from an administration of type I interferon. This finding enables to personalize patient's treatment methods on the grounds of the presence or absence of SNP rs9984273 (C/T) in IFNAR2. The presence or absence of SNP rs9984273 (C/T) in IFNAR2 may be determined simply by using a specific genomic test and the result of the test may be utilized to estimate outcome and response in a disease or a disorder requiring intervention with type I interferon.

Further, it has been observed that concomitant corticosteroid uses with type I interferons, such as interferon alpha or interferon beta, does not affect the treatment response in the patients having SNP rs9984273 (C/T) in IFNAR2. In patients having SNP rs9984273 (C/T) in IFNAR2 has responsiveness to type I interferon, such as interferon alpha or interferon beta pharmacological intervention despite concomitant corticosteroid use. The presence of SNP rs9984273 (C/T) in IFNAR2 in patient provides a treatment method to up-regulate CD73 by using type I interferon despite concomitant corticosteroid use. The presence of SNP rs9984273 (C/T) in IFNAR2 in patient can also be used as a marker to aid a clinical decision making to start or not to start an administration of corticosteroids in a combination with type I interferon treatment.

According to one aspect of the present invention a combination of genetic test and type I interferon treatment can be used in the prevention and/or treatment of acute organ injuries (ARDS, AKI, SIRS and MOF) and severe viral infections. One such treatment is intravenous interferon beta-1a, which is considered to be beneficial e.g. in the treatment of acute organ injuries (ARDS, AKI, SIRS and MOF) and severe viral infections.

According to another aspect of the present invention, a combination of genetic test and type I interferon treatment can be used in the prevention and/or treatment of vascular-endothelial diseases in humans with sepsis, severe acute viral infections, humans undergoing major cardiovascular surgery leading to ischemia-reperfusion injury, and disease states referred to as AKI, ARDS, SIRS, MOF, as well as MS.

According to yet another aspect of the present invention, a combination of genetic test and type I interferon treatment can be used in the prevention and/or treatment of malignant diseases in humans comprising hairy cell leukaemia, malignant melanoma, follicular lymphoma, condylomata acuminate, AIDS related Kaposi's Sarcoma, chronic hepatitis C, acute hepatitis C, and chronic hepatitis B.

According to the present invention SNP rs9984273 (C/T) and/or a SNP in linkage disequilibrium with the SNP rs9984273 (C/T) in IFNAR2 can be used as prognostic biomarker in the above-mentioned conditions/diseases.

BRIEF DESCRIPTION OF THE DRAWINGS

FIGS. 4 and 5 shows the results of a multivariable logistic regression model of the phase III clinical study.

DETAILED DESCRIPTION OF THE INVENTION

Terms and Definitions

The term "patient" or "individual" refers to a human.

The term "treatment" or "treating" shall be understood to include complete curing of a disease as well as amelioration or alleviation of said disease.

The term "prevention" shall be understood to include complete prevention, prophylaxis, as well as lowering the individual's risk of falling ill with said disease or disorder.

Discovery of the Invention

In a large-scale phase III randomized placebo-controlled study investigating the use of intravenous interferon beta-1a to treat acute respiratory distress syndrome (ARDS), it was not found to be superior to placebo.

Figure 1:
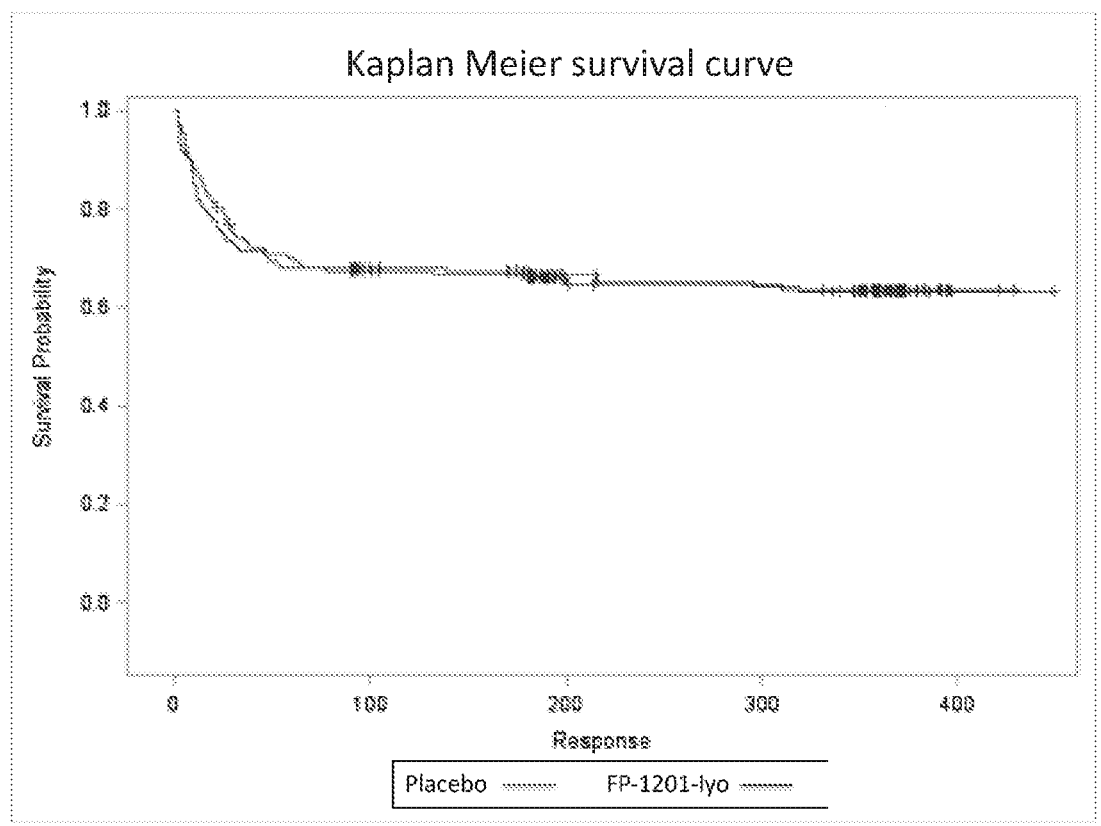
FIG. 1 shows Kaplan-Meier survival curves of ARDS patients receiving intravenous interferon-beta-1a (FP-1201-lyo) or placebo in the phase III clinical study.

The protocol of the study is more detailed described in Bellingan et. al. 2017. The Phase III trial study was performed as double-blind, 1 to 1 randomised, parallel-group trial, in which the efficacy and safety of recombinant human interferon beta-1a administered intravenously were studied compared with placebo in the treatment of adult patients with ARDS. The study, which recruited 300 patients, was conducted in 64 hospital intensive care units (ICU) in Belgium, the Czech Republic, Finland, France, Germany, Italy, Spain and the UK. Patients were randomly assigned to receive 10 µg recombinant human interferon beta-1a or placebo administered intravenously once daily for 6 days and monitored for 28 days or until discharged from the intensive care unit. The primary endpoint was a composite endpoint including any cause of death at 28 days and days free of mechanical ventilation within 28 days among survivors. In the study, the treatment with recombinant human interferon beta-1a did not result in a reduced mortality rate, or an increased number of ventilator free days compared to placebo, although the earlier phase I/II studies were showed on the reduced mortality. The Kaplan-Meyer survival curve of the trial results is presented in FIG. 1. Therefore, more detailed analysis of the study results and treated patients are now performed.

Figure 3A:
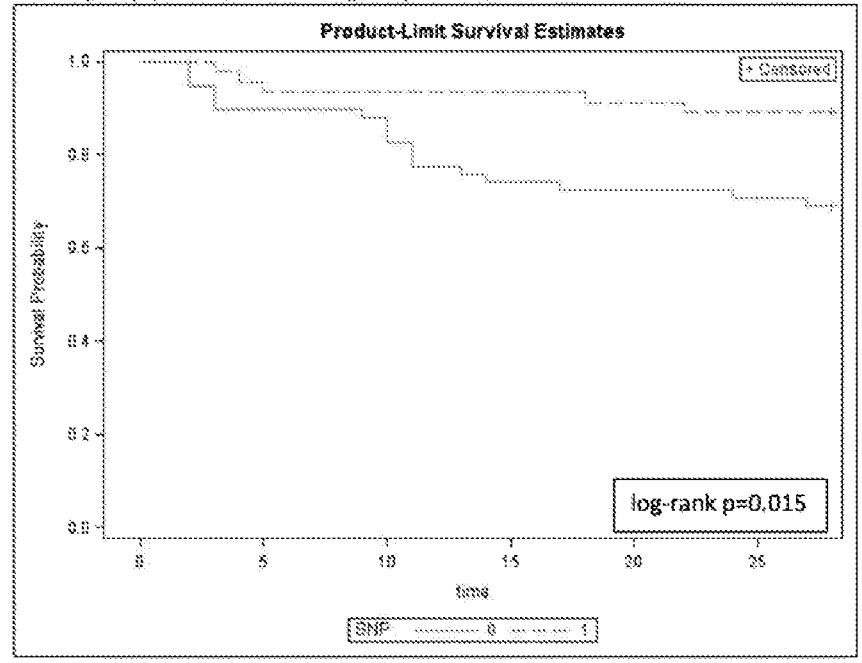
FIGS. 3a and 3b shows Kaplan-Meier survival curves of ARDS patients receiving intravenous interferon-beta-1a with or without the (SNP) rs9984273 (C/T) in IFNAR2 in the phase III clinical study (0=no polymorphism, 1=polymorphism present)
Figure 3B:
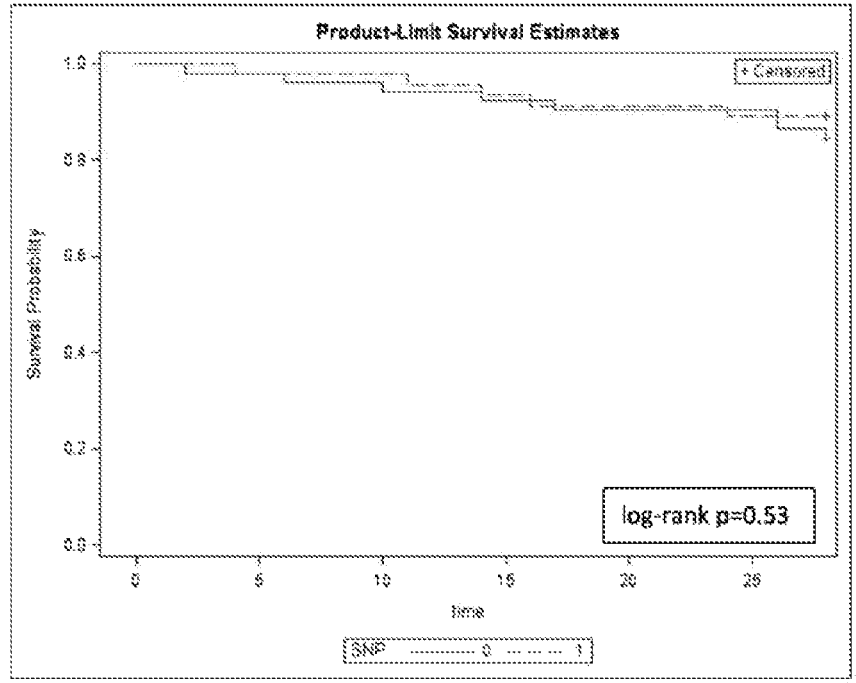

For more detailed analysis of the phase III randomized placebo-controlled study results, it has been observed that the study subjects receiving intravenous interferon beta-1a and having single nucleotide polymorphism (SNP) rs9984273 (C/T) in subunit 2 of the interferon alpha and beta receptor (IFNAR2) had a significantly better outcome than did the subjects receiving interferon treatment without said SNP rs9984273 (C/T), as shown in FIG. 3a. This was not seen in the placebo group presented in FIG. 3b. Outcome of subjects in the placebo group did not differ whether they had said SNP rs9984273 (C/T) or not. Further, as explained in detail below, in a multivariable logistic regression model adjusted for disease severity it was shown that the simultaneous administration of corticosteroids was independently associated with mortality, while the combination of the SNP rs9984273 (C/T) and interferon treatment had very significant effect on survival.

For analyzing more detailed the results of the above described phase III randomized placebo-controlled study a linear stepdown multivariable regression model was performed to investigate what are the most significant factors affecting outcome at day 28 (D28) after starting the treatment. Variables included in the model were selected according to univariate analyses. Variables with a test P value <0.15 were entered into the model. These were the overlapping use of corticosteroids during the treatment period of interferon beta (i.e. from day 0 to 7) in the trial study, and presence of C/T polymorphism in subunit 2 of the interferon alpha and beta receptor (INFAR2, polymorphism ID: rs9984273). Continuous numeric APACHE II score was used to adjust for disease severity since it also had a correlation with mortality in univariate analyses.

The results of a multivariable logistic regression model of the phase III study are presented in FIGS. 4 and 5. Tables presented in FIG. 4 are from patient group treated with interferon, and tables presented in FIG. 5 are from patient group treated with placebo. In Tables, SNP: 1=gene present, 0=gene not present and corticosteroid effect: cstart2=corticosteroid adjusted during dosing, adjusted for APACHE score (AP30).

The multivariate regression model shows that patients receiving interferon beta-1a treatment and carrying the SNP rs9984273 (C/T) were 5.7 times greater likelihood to be alive at D28 (p=0.0057) than patients without said mutation, while patients receiving corticosteroid (cstart2) during the treatment period were 7.6 times greater likelihood to be dead at D28 (odds ratio 0.13, p=0.0008). A similar detrimental effect for the use corticosteroid during the first days of treatment was seen in the placebo group (3.5 times greater likelihood to be dead at D28, p=0.06), but no survival effect was seen for the C/T polymorphism in the placebo group. This means that together the C/T polymorphism in subunit 2 of the interferon alpha and beta receptor (INFAR2, polymorphism ID: rs9984273) and interferon beta-1a treatment is the most favorable combination for patient outcome and interferon treatment efficacy, i.e. the most predictive value of survival is the combination of having the defined SNP and receiving type I interferon treatment.

Embodiments of the Invention

As presented above, the finding of the present invention provides a method for classifying a patient as being more likely to respond to type I interferon therapy.

A method for determining a patient's responsiveness to a therapy comprising administration of type I interferon and optionally concomitant administration of corticosteroids, comprises
  obtaining a sample from a patient,
  determining the presence or absence of single nucleotide polymorphism (SNP) rs9984273 (C/T) in subunit 2 of the interferon alpha and beta receptor (IFNAR2) in chromosome 21 of the patient from the sample obtained from the patient, and
  classifying the patient on the grounds of the presence or absence of said SNP, wherein
    i) the presence of said SNP indicates responsiveness to the therapy, which comprises an administration of type I interferon to said patient with or without concomitant administration of corticosteroids, or
    ii) the absence of said SNP indicates non-responsiveness to the therapy with concomitant administration of corticosteroids and modest responsiveness to said therapy without concomitant administration of corticosteroids.

A method according to an embodiment of the invention for determining a patient's responsiveness to a therapy comprising a treatment with type I interferon concomitant with a corticosteroid comprises
  determining the presence or absence of single nucleotide polymorphism (SNP) rs9984273 (C/T) in subunit 2 of the interferon alpha and beta receptor (IFNAR2) in chromosome 21 from a sample obtained from the patient, and
  classifying the patient on the grounds of the presence or absence of said SNP, wherein
    i) the presence of said SNP indicates responsiveness to the therapy, which comprises the treatment with type I interferon and the corticosteroid, or
    ii) the absence of said SNP indicates non-responsiveness to the therapy which comprises the treatment with type I interferon and the corticosteroid.

Figure 2:
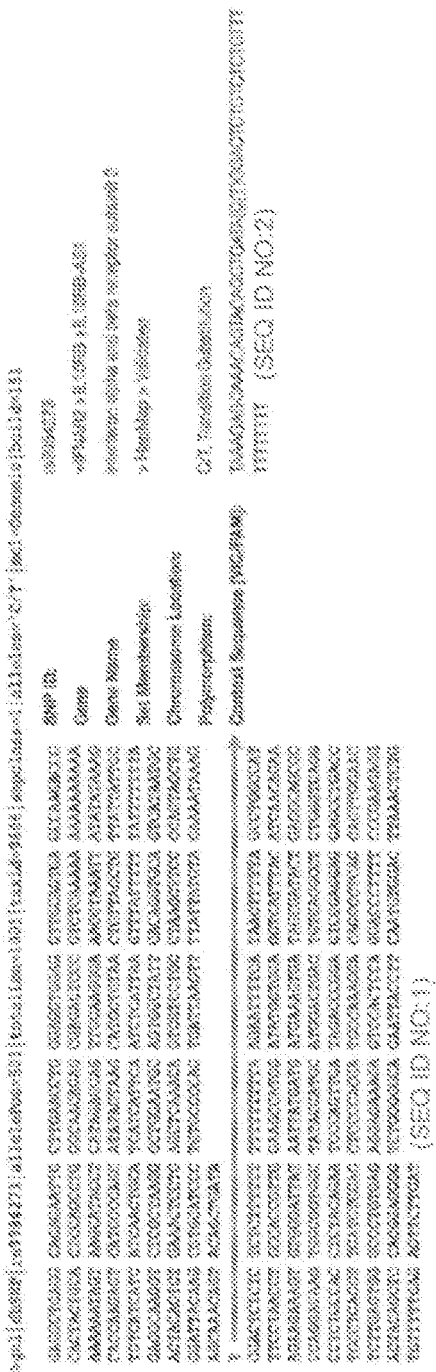
FIG. 2 shows the single nucleotide polymorphism (SNP) rs9984273 (C/T) in IFNAR2 (SEQ ID NO:1) specified as the decisive factor according to the present invention to make the clinical decision to treat or not to treat a patient with type I interferons. Context Sequence [VIC/FAM] used in the analysis is shown in SEQ ID NO:2.

A method according to the present invention is simply based on the determining the presence or absence of single nucleotide polymorphism (SNP) rs9984273 (C/T) in the sample drawn from the patient. The SNP rs9984273 (C/T) in question is situated in subunit 2 of the interferon alpha and beta receptor (IFNAR2) in chromosome 21 (*Homo sapiens*: chr 21: chr position 34635065). It is fully referenced in PubMed See ncbi.nlm.nih.gov/projects/SNP/snp_ref.cgi?rs=9984273) and prior to this no functional role has been discovered for this SNP. A detailed description of the position of the single nucleotide polymorphism (C/T) in question on subunit 2 of the interferon alpha and beta receptor (IFNAR2) in chromosome 21 is also presented in FIG. 2. Patient having said SNP rs9984273 (C/T) having C instead of T at least in one of said genes.

The presence or absence of SNP rs9984273 (C/T) in the sample can be analyzed by detecting a SNP rs9984273 (C/T) and/or a SNP in linkage disequilibrium with the SNP rs9984273 (C/T), in subunit 2 of the interferon 30 alpha and beta receptor (IFNAR2) in chromosome 21. According to an embodiment of the present invention, the presence or absence of SNP rs9984273 (C/T) and/or a SNP in linkage disequilibrium with the SNP rs9984273 (C/T) in the sample can be determined on commercially available assays and measurement methods. The present invention is not restricted to 35 any specific method or assay, but all suitable assays and/or methods can be utilized for amplifying and detecting said SNPs in genomic DNA samples. Genomic DNA may originate from a variety of the sample types derived from the patient, such as tissue, saliva, blood or serum samples. The presence of said SNP may be determined e.g. by contacting the sample with the oligonucleotide probes recognizing a SNP rs9984273 (C/T) and/or a SNP in linkage disequilibrium with the SNP rs9984273 (C/T). For more detailed analysis of the patient group of the above described phase III study, the presence of SNP rs9984273 (C/T) was detected by using Taqman® SNP genotyping assay (ThermoFisher Scientific; Assay ID C_2443264_10). More detailed information is presented in thermofisher.com/order/genome-database/details/genotyping/C 2443264_10?CID=MCID=&subtype=. Predesigned TaqMan® SNP Genotyping Assay includes two allele-specific TaqMan® probes containing distinct fluorescent dyes and a PCR primer pair to detect specific SNP targets. The present invention is not restricted to this specifically mentioned assay method for recognizing said SNP. According to another embodiment of the present invention, the presence of said SNPs may be determined by contacting the sample with the oligonucleotide probes, utilizing polymerase chain reaction and a specific restriction enzyme recognizing the polymorphic SNP rs9984273 (C/T) and/or a SNP in linkage disequilibrium with the SNP rs9984273 (C/T). Suitable probes may differ from e.g. by a length of sequence to be detected.

The presence or absence of SNP rs9984273 (C/T) in the sample can be determined by detecting a SNP rs9984273 (C/T) as such by using suitable probes. Alternatively, the presence or absence of SNP rs9984273 (C/T) in the sample may be determined by detecting a SNP in linkage disequilibrium with the SNP rs9984273 (C/T). A linkage disequilibrium means that the two (or more) polymorphisms are present at the same time (with a probability of more than 50%) in a genetic sample. Also meaning that the physical distance between the two (or more) different loci of these polymorphisms in linkage disequilibrium is short meaning that these loci are not inherited independently from each other, but with a high probability (>50%) they are inherited together. Therefore, the screening method of the patients may comprises determining the presence or absence of single nucleotide polymorphism (SNP) in the sample, which SNP is a SNP rs9984273 (C/T) and/or a SNP in linkage disequilibrium with the SNP rs9984273 (C/T) in IFNAR2.

When the presence of SNP rs9984273 (C/T) has detected from the patient, it indicates patient's responsiveness to the therapy, which comprises an administration of type I interferon to said patient with or without concomitant administration of corticosteroids. Whereas, the absence of said SNP in the sample indicates non-responsiveness to the therapy with concomitant administration of corticosteroids and modest responsiveness to said therapy without concomitant administration of corticosteroids, i.e. if the patient which has not SNP rs9984273 (C/T) is treated by type I interferon, it should be done without corticosteroid. By determining the presence or absence of said SNP, the doctor can be to decision to start or not to start an administration of type I interferon. Further, said SNP can also be used as a marker to aid a clinical decision making to start or not to start an administration of corticosteroids in a combination with type I interferon treatment.

According to the present invention, the patient with the presence of SNP rs9984273 (C/T) in the sample has the survival probability of >0.8, preferably >0.85 or more preferably >0.9 with the therapy comprising an administration of type I interferon to said patient with or without concomitant administration of corticosteroids. Therefore, the screening method according to the present invention improves remarkably patients' possibilities to survive since the treatment can be personalized as early stage of the therapy.

In this application the term type I interferon refers to all forms of interferon beta and interferon alpha and their subtypes. In a preferred embodiment according to the invention interferon beta may be interferon beta-1a, interferon beta-1b and/or interferon beta-2 (i.e. Interleukin-6). In one preferred embodiment according to the present invention, type I interferon comprises interferon beta-1a. In an embodiment according to the invention interferon alpha may be selected from interferon alpha-1, interferon alpha-2, interferon alpha-8, interferon alpha-10, interferon alpha-14 and interferon alpha-21. The screening method according to the invention is assumed to be applicable to screen any patient suffering from the disease of disorder requiring or beneficiating from a pharmacological intervention with type I interferon.

According to an embodiment of the present invention, when therapy comprises also an administration of corticosteroids in combination with type I interferon, the corticosteroid is selected from the group of glucocorticoids. According to an embodiment of the present invention glucocorticoid may be hydrocortisone, prednisone, prednisolone, methylprednisolone, betamethasone and/or dexamethasone.

According to the present invention, a composition comprising type I interferon as an active ingredient is used in prevention and/or treatment of the disease or the disorder in an individual, which disease or disorder requiring or beneficiating from type I interferon pharmacological intervention. According to an embodiment of the present invention pharmaceutical preparations of the compositions comprise also suitable pharmaceutically acceptable carriers comprising excipients and auxiliaries that facilitate processing of the active compounds into preparations that can be used pharmaceutically. The compositions comprise a pharmacologically effective amount of type I interferon. The expression "pharmacologically effective amount" is meant to include any amount of type I interferon that is sufficient to bring about a desired therapeutically result. The therapeutic effect may depend on the genetic profile of the subject. The pharmaceutical compositions according to the present invention can be administered by any means that achieve their intended purpose. For example, administration can be intravenous, intraarticular or subcutaneous.

The present invention is based to type I interferon pharmaceutical treatment together with a genetic test to made prior the treatment decision. The specified genetic test can also be used to predict patient outcome and need of interferon intervention in disease states requiring a natural type I interferon response such as severe life threatening viral infections, e.g. EBOLA, MERS, influenza, avian flu, swine flu, and other similar conditions leading to a systemic inflammatory response syndrome (SIRS) and dysfunction of central organs, namely acute kidney injury (AKI), acute respiratory distress syndrome (ARDS) and/or multi-organ failure (MOF); as well as ischemic and systemic inflammatory insults brought forth by major trauma, multiple transfusions or cardiovascular surgery, e.g. open aortic reconstruction, open heart surgery, organ transplantation or any other surgical intervention requiring extracorporeal circulation and cross clamping of major arteries.

The invention comprising an administration of type I interferon may be used to treat a range of vascular-endothelial diseases in humans. The CD73, an endothelial ectoenzyme, which can produce local adenosine, is a key molecule to maintain endothelial barrier and lung function. Interferon-beta increases CD73 expression resulting in increased local adenosine. Many inflammatory conditions are known to result in the loss of CD73 from the surfaces of inflamed/injured endothelial cells, therefore reducing available adenosine content. The anti-inflammatory properties of adenosine are well known in the literature and any condition that is known to result from the loss of local adenosine effect will benefit from the up-regulation of CD73 expression. If permanent help is needed, the up-regulation of CD73 should be based on de novo synthesis.

The invention comprising an administration of type I interferon is also suitable for use in the prevention and/or treatment of ischemia-reperfusion injury resulting from vascular or cardiac surgery, organ transplantation, stroke, myocardial infarction or acute coronary syndrome, or for use in ischemic pre-conditioning prior to major vascular or cardiac surgery and organ transplantation. In addition, the invention is suitable for use in the prevention and/or treatment of ischemia-reperfusion injury in myocardial infarction and stroke.

The invention comprising an administration of type I interferon is suitable for use in severe bacterial pneumonia and sepsis leading to a systemic inflammatory response syndrome (SIRS) and multi-organ failure (MOF).

The invention comprising an administration of type I interferon is suitable for use in severe viral respiratory or haemorrhagic infections leading to a systemic inflammatory response syndrome (SIRS) and multi-organ failure (MOF).

The invention comprising an administration of type I interferon is suitable for use in treating multiple sclerosis (MS).

The invention comprising an administration of type I interferon, especially administration of interferon alpha, is suitable for use, in treating malignant diseases in humans comprising hairy cell leukaemia, malignant melanoma, follicular lymphoma, condylomata acuminate, AIDS related Kaposi's Sarcoma, chronic hepatitis C, acute hepatitis C, and chronic hepatitis B.

According to an embodiment of the invention, the disease or the disorder requiring or beneficiating from type I interferon pharmacological intervention may be selected from vascular-endothelial diseases, acute respiratory distress syndrome (ARDS), systemic inflammatory response syndrome (SIRS), or other traumatic conditions, ischemia-reperfusion injury, ischemic pre-conditioning prior to major vascular or cardiac surgery and organ transplantation, acute pancreatitis, acute kidney injury, multi-organ failure (MOF), severe respiratory or haemorrhagic viral infections, and multiple sclerosis (MS).

In one of the embodiments of the method of treating a patient described herein, the patient has vascular-endothelial disease, or any other condition described in the present application. The administration of type I interferon should start as early as possible after disease diagnosis and genetic testing.

According to an embodiment of the present invention, a method for determining a patient's responsiveness to the therapy comprising administration of type I interferon and optionally concomitant administration of corticosteroids is used to screen patients suffering ARDS and enabling to personalize treatment methods on the grounds of the presence or absence of SNP rs9984273 (C/T) in IFNAR2.

A method according to an embodiment of the present invention for treating a patient by a therapy comprising administration of type I interferon and optionally concomitant administration of corticosteroids comprises determining the presence or absence of SNP rs9984273 (C/T) in IFNAR2 from a sample obtained from the patient, and administering a composition comprising type I interferon, optionally with or without a corticosteroid. A treating method according to the present invention comprises administering to the patient a) a composition comprising type I interferon with or without a corticosteroid when the presence of said SNP has been detected, or b) a composition comprising type I interferon without a corticosteroid when the absence of said SNP has been detected.

Patients will receive an effective amount of the type I interferon as the principal active ingredient i.e. an amount that is sufficient to treat, ameliorate, or prevent the disease or disorder in question. The optimum effective amount and concentration of type I interferon for any particular subject will depend upon various factors, including the patient's age, size, health and/or gender, the nature and extent of the condition, and also on any possible further therapeutic(s) administered in combination with type I interferon for example the simultaneous administration of corticosteroids, which are noticed to interfere with interferon activity. The effective amount delivered for a given situation may be determined with in the judgment of a clinician and the genetic test performed.

REFERENCES CITED IN THE DESCRIPTION

Bellingan et. al. The effect of intravenous interferon-beta-1a (FP-1201) on lung CD73 expression and on acute respiratory distress syndrome mortality: an open-label study. Lancet Respir Med 2014, 2: 98-107.

Bellingan et. al. Comparison of the efficacy and safety of FP-1201-lyo (intravenously administered recombinant human interferon beta-1a) and placebo in the treatment of patients with moderate or severe acute respiratory distress syndrome: study protocol for a randomized controlled trial. Trials 2017, 18:536.

Jalkanen, S. and Salmi, M., VAP-1 and CD73, Endothelial cell surface enzymes in leukocyte extravasation. Arterioscler. Thromb. Vasc. Biol. 2008, 18-26.

Kiss et. al., IFN-β protects from vacular leakage via up-reguölation of CD73. Eur. J. Immunology 2007, 37: 3334-3338.

Levy et. al., Ringing the interferon alarm: differential regulation of gene expression at the interface between innate and adaptive immunity. Current Opinion in Immunology 2003, 15:52-58.

Mahurkar et. al., Response to interferon-beta treatment in multiple sclerosis patients: a genome-wide association study. The Pharmacogenomics Journal, March 2016, 1-7.

The invention claimed is:

1. A method for treating a patient by a therapy comprising administration of type I interferon and optionally concomitant administration of corticosteroids, comprising
    obtaining a sample from the patient,
    detecting SNP rs9984273 (C/T) in subunit 2 of the interferon alpha and beta receptor (IFNAR2) in chromosome 21, wherein T is replaced by C, in said sample, and
    administering to the patient a) a composition comprising type I interferon with or without a corticosteroid when said SNP has been detected, or b) a composition comprising type I interferon without a corticosteroid when said SNP has not been detected.

2. The method according to claim 1, wherein the patient is suffering from a disease or a disorder selected from the group consisting of
    vascular-endothelial diseases,
    acute respiratory distress syndrome (ARDS), systemic inflammatory response syndrome (SIRS), or other traumatic conditions,
    ischemia-reperfusion injury,
    ischemic pre-conditioning prior to major vascular or cardiac surgery and organ transplantation,
    acute pancreatitis,
    acute kidney injury,
    multi-organ failure (MOF),
    severe respiratory or haemorrhagic viral infections,
    multiple sclerosis (MS),
    hairy cell leukaemia, malignant melanoma, follicular lymphoma, condylomata acuminate, AIDS related Kaposi's Sarcoma, chronic hepatitis C, acute hepatitis C and chronic hepatitis B.

3. The method according to claim 1, wherein the patient has acute respiratory distress syndrome (ARDS).

4. A method for administering type I interferon to a patient in need of such treatment, with concomitant administration of corticosteroids, comprising
    a) obtaining a sample from a patient,
    b) detecting single nucleotide polymorphism (SNP) rs9984273 (C/T) in subunit 2 of the interferon alpha and beta receptor (IFNAR2) in chromosome 21, wherein T is replaced by C, in the sample obtained from said patient, and
    c) administering type I interferon to said patient with concomitant administration of corticosteroids after single nucleotide polymorphism (SNP) rs9984273 (C/T) in subunit 2 of the interferon alpha and beta receptor (IFNAR2) in chromosome 21 has been detected.

5. The method according to claim 4, wherein the type I interferon is selected from the group consisting of interferon beta, interferon alpha and any subtypes of interferon beta and interferon alpha.

6. The method according to claim 5, wherein type I interferon is interferon beta-1a.

7. The method according to claim 4, wherein the corticosteroid is a glucocorticoid.

8. The method according to claim 7, wherein said glucocorticoid is selected from the group consisting of hydrocortisone, prednisone, prednisolone, methylprednisolone, betamethasone and dexamethasone.

9. The method according to claim 4, wherein the patient is suffering from a disease or a disorder selected from the group consisting of
    vascular-endothelial diseases,
    acute respiratory distress syndrome (ARDS), systemic inflammatory response syndrome (SIRS), or other traumatic conditions,
    ischemia-reperfusion injury,
    ischemic pre-conditioning prior to major vascular or cardiac surgery and organ transplantation,
    acute pancreatitis,
    acute kidney injury,
    multi-organ failure (MOF),
    severe respiratory or haemorrhagic viral infections,
    multiple sclerosis (MS),
    hairy cell leukaemia,
    malignant melanoma,
    follicular lymphoma,
    condylomata acuminate,
    AIDS related Kaposi's Sarcoma,
    chronic hepatitis C,
    acute hepatitis C, and
    chronic hepatitis B.

10. The method according to claim 4, wherein the patient has acute respiratory distress syndrome (ARDS).

11. The method according to claim 4, wherein the patient has a survival probability of >0.8 when said SNP has been detected in the sample.

12. The method according to claim 11, wherein the patient has a survival probability of >0.85.

13. The method according to claim 12, wherein the patient has a survival probability of >0.9.

* * * * *

```
SEQUENCE LISTING

<160> NUMBER OF SEQ ID NOS: 2

<210> SEQ ID NO 1
<211> LENGTH: 1001
<212> TYPE: DNA
<213> ORGANISM: Homo sapiens

<400> SEQUENCE: 1
gaggctgagg cagagaattg cttgaacctg ggaggtggag gttgcagtga gccaagaccg      60
cactactgca ctccagcctg ggcaacagag cgagactccc gtctcaaaaa aaaaaaaaaa     120
aaaaaatagt aagcatacct catagagcag ttgcaaggga aagtaaatt atatataaag      180 caccaagagt catgcccagc atatagtaag catggtgtaa ctgttagctg ttattattgc     240
tgtcatcatc atcaactgca tcatcattca atctcattaa gtttatttt tatttttta      300 gaggcaaggt ctcgctaagg gctggaatgc agtggctatt cacaggtgca gtcataatgc     360
actacagtct gaaactcctg agctcaaaca gtcgtcctgc ctaagcttcc ccagtagctg     420
ggattacaag cgtgcatccc tgtgcccag tgattaagtt ttattatgta gaaataaag      480 agcaaacagt acagctgata yggactctct ctctctttt tttttttttt aagaattttc     540 ataactttt agcctggcca tttcctaacc tgccaccgtt ggaagccatg gatatggtgg     600
aggtcattta catcaacaga aagaagaaag tgtgggatta taattatgat gatgaaagtg     660
atagcgatac tgaggcagcg cccaggacaa gtggcggtgg ctataccatg catggactga     720
ctgtcaggcc tctgggtcag gcctctgcca cctctacaga atcccagttg atagacccgg     780
agtccgagga ggagcctgac ctgcctgagg ttgatgtgga gctccccacg atgccaaagg     840
acagccctca gcagttggaa ctcttgagtg ggccctgtga gaggagaaag agtccactcc     900
aggacccttt tcccgaagag gactacagct ccacggaggg gtctgggggc agaattacct     960
tcaatgtgga cttaaactct gtgttttga gagttcttga t                        1001

<210> SEQ ID NO 2
<211> LENGTH: 51
<212> TYPE: DNA
<213> ORGANISM: Homo sapiens

<400> SEQUENCE: 2
taaagagcaa acagtacagc tgatayggac tctctctctc tttttttttt t              51
```